(12) United States Patent
Kowalski et al.

(10) Patent No.: US 7,704,453 B2
(45) Date of Patent: Apr. 27, 2010

(54) METHOD FOR ESTABLISHING A STERILIZING DOSE FOR RADIATION SENSITIVE PRODUCTS

(75) Inventors: John B. Kowalski, Somerville, NJ (US); Stephen C. Yeadon, Hampton, NJ (US)

(73) Assignee: Ethicon, Inc., Somerville, NJ (US)

( * ) Notice: Subject to any disclaimer, the term of this patent is extended or adjusted under 35 U.S.C. 154(b) by 219 days.

(21) Appl. No.: 11/759,279

(22) Filed: Jun. 7, 2007

(65) Prior Publication Data

US 2008/0305001 A1 Dec. 11, 2008

(51) Int. Cl.
*A61L 2/00* (2006.01)
*G01T 1/00* (2006.01)
(52) U.S. Cl. ........................................... 422/22
(58) Field of Classification Search ................ None
See application file for complete search history.

(56) References Cited

U.S. PATENT DOCUMENTS

| | | | |
|---|---|---|---|
| 5,362,442 | A | 11/1994 | Kent |
| 6,171,549 | B1 | 1/2001 | Kent |
| 6,346,216 | B1 | 2/2002 | Kent |
| 6,455,013 | B1 | 9/2002 | Crihan |
| 6,635,222 | B2 | 10/2003 | Kent |
| 6,682,694 | B2 | 1/2004 | Trinh et al. |
| 6,682,695 | B2 | 1/2004 | MacPhee et al. |
| 6,916,911 | B1 | 7/2005 | Bar et al. |
| 6,946,098 | B2 | 9/2005 | Miekka et al. |
| 7,125,569 | B2 | 10/2006 | Nur et al. |
| 2006/0280645 | A1 | 12/2006 | Sellers et al. |
| 2007/0084145 | A1 | 4/2007 | Scheerer |
| 2007/0092959 | A1 | 4/2007 | Nur et al. |
| 2007/0111196 | A1 | 5/2007 | Alarcon et al. |

FOREIGN PATENT DOCUMENTS

| | | |
|---|---|---|
| EP | 1390485 B1 | 10/2006 |
| EP | 1785153 A2 | 5/2007 |

OTHER PUBLICATIONS

Hilmy, N., Basril, A. and Febrida, A., Indonesia: Statistical sampling technique in validation of radiation sterilisation dose of biological tissue. Cell and Tissue Banking, 4: 185-191, 2003.*

Kowalski, J.B. and Tallentire, A. Substantiation of 25 kGy as a sterilization dose: a rational approach to establishing verification dose. Radiation Physics and Chemistry, 54: 55-61, 1999.*

Davis, K.W., Strawderman, W.E. and Whitby, J.L., The rationale and a computer evaluation of a gamma irradiation sterilizatin dose determination method for medical device using a substerilization incremental dose sterility test protocol. Journal of Applied Bacteriology 57: 31-50, 1984.*

Association for the Advancement of Medical Instrumentation 'Sterilization of Health Care Products-Radiation Sterilization-Substantiation of 25 kGy as a Sterilization Dose-Method $VD_{max}$,' Technical Information Report 27:2001.

Association for the Advancement of Medical Instrumentation 'Process Control Guidelines for Gamma Radiation Sterilization of Medical Devices' RS-3/84.

Davis, K.W., et al "DS Gamma Radiation Dose Setting and Auditing Strategies for Sterilizing Medical Devices" Sterilization of Medical Products. Montreal: Multiscience Publications Ltd. (1981) vol. 2, pp. 34-102.

Davis, K.W., et al "The Rationale and a Computer Evaluation of a Gamma Irradiation Sterilization Dose Determination Method for Medical Devices Using a Substerilization Incremental Dose Sterility Test Protocol", Journal of Applied Bacteriology. (1984) vol. 57, pp. 31-50.

Harries, J. "Requirements for the Validation and Routine Control of Radiation Sterilization of Healthcare Products—A Discussion of Current Revisions" Business Briefing: Medical Device Manufacturing & Technology. (2005) pp. 23-25.

Hilmy, N., et al 'Indonesia: Statistical Sampling Technique in Validation of Radiation Sterilisation Dose of Biological Tissue' Cell and Tissue Banking. (2003) vol. 4, pp. 185-191.

(Continued)

*Primary Examiner*—Elizabeth L McKane
*Assistant Examiner*—Regina Yoo
(74) *Attorney, Agent, or Firm*—T

(57) ABSTRACT

A method provides for sterilizing with radiation objects which have a low bioburden and which are sensitive to radiation. A dosage of radiation sufficient to ensure sterilization without damaging the object is determined by determining the bioburden upon one or more samples of the objects, determining an estimate of the dose that results in a probability of 0.01 of a surviving microorganism by testing a quantity of samples of the objects at varying dosage levels of radiation, confirming the estimate by testing a quantity of samples of the objects at the dose that was estimated; and calculating a dosage for the sterility assurance level of 10-6 by adding a factor to the dose that was confirmed to result in a probability of 0.01 of a surviving microorganism and wherein the factor is proportional to the dose that yields a probability of 0.01 of a surviving microorganism and inversely proportional to a log of the bioburden.

16 Claims, No Drawings

OTHER PUBLICATIONS

Kowalski, J.B., et al 'Aspects of Putting into Practice $VD_{max}$' Radiation Physics and Chemistry. (2003) vol. 67, pp. 137-141.

Kowalski, J.B., et al "Field Evaluations of the $VD_{max}$ Approach for Substantiation of a 25 kGy Sterilization Dose and Its Application to Other Preselected Doses" Radiation Physics and Chemistry. (2002) vol. 64, pp. 411-416.

Kowalski, J.B., et al "Radiation Sterilization—Evaluation of a New Approach for Substantiation of 25 kGy" Radiation Physics and Chemistry. (2000) vol. 58, pp. 77-86.

Kowalski, J.B., et al "Substantiation of 25 kGy as a Sterilization Dose: A Rational Approach to Establishing Verification Dose" Radiation Physics and Chemistry. (1999) vol. 54, pp. 55-64.

Tallentire, A., et al "Microbiological Quality Control of Sterilized Products: Evaluation of a Model Relating Frequency of Contaminated Items with Increasing Radiation Treatment", Journal of Applied Bacteriology (1971) vol. 34, No. 3, pp. 521-534.

Tallentire, A., et al "The Sub-Process Dose in Defining the Degree of Sterility Assurance" *Sterilization by Ionizing Radiation* (1978) vol. 2, pp. 65-80.

Whitby, J.L., et al "Use of Incremental Doses of Cobalt 60 Radiation as a Means to Determine Radiation Sterilization Dose" Journal of the Parenteral Drug Association. (1979) vol. 33, No. 3, pp. 144-155.

International Search Report re: PCT/US2008/065598 dated Oct. 1, 2008.

\* cited by examiner

METHOD FOR ESTABLISHING A STERILIZING DOSE FOR RADIATION SENSITIVE PRODUCTS

BACKGROUND OF THE INVENTION

The present invention relates to radiation sterilization and more particularly to determining a minimal, yet effective, radiation dosage for sterilization.

Dose setting Methods 1 and 2, used for the validation of a radiation sterilization dose, were developed in the early 1980's. At that time, 2.5 megarads (25 kGy) was viewed as a generally acceptable dose for the sterilization of medical devices. It was recognized, however, that many medical devices would have a sterility assurance level (SAL) of $10^{-6}$ at lower doses and some would require a dose greater than 25 kGy to attain this SAL. Important characteristics of the medical devices used in the developmental work for Methods 1 and 2 were their manufacture in minimally controlled environments, resulting in relatively higher levels and diversity of types of bioburden, and materials of construction that were relatively unaffected by radiation doses of 25 to 75 kGy.

Many health care products that are currently in development differ significantly from those produced in the early 1980's in that they have one or more bioactive components that are relatively sensitive to radiation damage and they are manufactured in a highly controlled environment which limits the numbers and types of contaminating microorganisms. Often, some or all of the components of these health care products are sterilized prior to introduction into the manufacturing process.

The key underlying principle of Methods 1 and 2 (see ISO 11137-2, 2006) is the use of direct testing of the radiation response of the product bioburden as part of the determination of a dose to attain an SAL of $10^{-6}$. With both methods, a test is performed where 100 product items are irradiated and a test of sterility is performed at a dose that is expected to result in ~1 nonsterile item ($10^{-2}$ SAL) out of the 100 items tested.

Method 2B is indicated for "low and consistent bioburden" but these qualitative terms are not strictly defined. With this method, no determination of product bioburden level is made and the radiation dose used for the 100 product items is estimated by the performance of an "incremental dose experiment" (IDE); this method uses an IDE with the following dose values: 1, 2, 3, 4, 5, 6, 7, and 8 kGy. Twenty product items are irradiated at each of these doses and subjected to a test of sterility. The purpose of the IDE is to identify the "first-fraction-positive" (FFP) dose, the first dose where at least one product item is found to be sterile and the remaining items nonsterile (such as 19/20 nonsterile).

The lowest dose in the IDE whose outcome is $0^+/20$ is an estimate of the dose that will yield a $10^{-2}$ SAL. One hundred product items are irradiated at this dose; this test is termed the "verification dose experiment" (VDE). If 0, 1, or 2 positive tests of sterility are observed in the VDE, the delivered dose is termed the "First-No-Positive" (FNP) dose. The determination of the FFP and FNP doses allows, in Method 2, for the calculation of a factor, termed "DS", that is used to derive a $10^{-6}$ sterilization dose from the experimentally determined $10^{-2}$ SAL dose.

The difficulty in applying Method 2B for current products with low average bioburden that are manufactured in highly-controlled environments is the manner in which the DS value is calculated. The use of the calculation "DS=1.6+[0.2(FNP−FFP)]" effectively puts a floor on the DS value equal to 1.8 kGy which yields a minimum sterilization dose of 8.2 kGy [sterilization dose=$10^{-2}$ dose+4(DS)=1.0+4(1.8)=8.2; FNP=1.0 kGy]. A sterilization dose of 8.2 kGy is overly conservative, for example, for a product with a bioburden of 1.0 composed of microorganisms that are relatively sensitive to radiation. The present invention overcomes the limitations of the methods in the current standards in determining an effective dose for radiation sensitive materials having low bioburdens.

SUMMARY OF THE INVENTION

A method, according to the present invention, provides for sterilizing objects with radiation. The method comprising the steps of determining a dosage of radiation sufficient to ensure sterilization to a sterility assurance level of $10^{-6}$ and then applying said dosage of radiation to the objects. The step of determining said dosage includes the steps of: determining a bioburden upon one or more samples of the objects; determining an estimate of the dose that results in a probability of 0.01 of a surviving microorganism by testing a quantity of samples of the objects at varying dosage levels of radiation to determine a dosage below which not at all samples are sterilized and above which they are sterilized; confirming the estimate of the dose that results in a probability of 0.01 of a surviving microorganism by testing a quantity of samples of the objects at the dose that was estimated; and calculating a dosage for the sterility assurance level of $10^{-6}$ by adding a factor to the dose that was confirmed to result in a probability of 0.01 of a surviving microorganism and wherein the factor is proportional to the dose that yields a probability of 0.01 of a surviving microorganism and inversely proportional to a log of the bioburden.

Preferably, the bioburden is equal or less than 20 CFU, and more preferably less than 5 CFU.

Preferably, the quantity is 100 samples of the objects for confirming that the estimated dose results in a probability of 0.01 of a surviving microorganism.

Preferably, the factor equals $PV*(CD/(2+ \log(BB))$, wherein PV represents a proportionality value, CD represents the dose that has been confirmed to result in a probability of 0.01 of a surviving microorganism and BB represents the bioburden in colony forming units. Preferably, PV ranges from 1.0 to 10.0. Preferably PV is 2 or greater, more preferably between 2 and 3, with 2.2 being most preferred.

In one aspect of the invention the object comprises a protein.

DETAILED DESCRIPTION OF THE INVENTION

A limitation to the use of radiation sterilization is the adverse effects that ionizing radiation may have on the product being irradiated. Similarly steam sterilization cannot be applied to heat-labile product. Heat may also be a limitation for ethylene oxide as well as effects produced from reaction with the gas itself. With modern technology, heat labile or otherwise process-sensitive product may be produced by aseptic processing to a level where a less than one-in-a-thousand items are contaminated. Such product cannot realistically achieve a $10^{-6}$ SAL through aseptic processing, but could, provided that product could stand the necessary radiation dose, be brought to a $10^{-6}$ SAL by a relatively low radiation dose.

The microbial world contains a vast number of species varying widely in their resistance to ionizing radiation. Although many are extremely sensitive there are some that are very radiation resistant, thus an essential element of any acceptable dose setting method is the inclusion in the process of a step that measures the radiation response of the product bioburden.

The present invention improves upon prior methods to determine $10^{-6}$ SAL product-specific sterilization dose that has an appropriate level of conservatism. It includes a determination of the bioburden to more accurately calculate sterilization doses in the presence of a low bioburden.

To determine the sterilization dose according to the present invention it is preferred to select at least 270 product items from each of three independent production batches of a product to be sterilized. The bioburden is determined for each of ten nonsterile selected product items from each batch including the average bioburden per item for each of the three batches and the average bioburden per item for all selected product items. It is preferred to determine the bioburden on individual product items but if the bioburden is too low it is possible to pull ten items from a single batch for the purpose of determining a batch average bioburden. Preferably, bioburden is determined following ISO 11737.

The average bioburden level for each of the three batches are compared to the overall average bioburden to determine whether any one of the batch averages is two or more time greater than the overall average bioburden. If one or more of the batch averages are two or more times higher than the overall average bioburden then for subsequent calculations the bioburden used should be the highest batch average, otherwise for subsequent calculations the overall average bioburden will be used.

An IDE is performed by irradiating twenty product items from one of the three production batches at one of a series of not less than eight doses increasing in nominal increments of 0.25 kGy starting at not less than 0.25 kGy. Each of these is monitored with dosimeters. Preferably, the dosages should be within a tolerance of +0.05 kGy or +10%, whichever is greater. The irradiated product items are then tested for sterility and the number of positive tests is noted. Preferably, such testing follows ISO 11737-2.

The FNP dosage is then determined. For each of the three batches the FNP dose is the lower of two consecutive doses at which all the tests of sterility are negative followed by no more than one further positive test in any of the remaining tests in the incremental dose series. Alternatively, FNP can be determined by finding the lowest dose at which one positive in 20 tests of sterility occurs immediately preceded by one and only one incremental dose at which all tests were negative and followed by incremental doses at which all tests are negative. This information is used to determine a "verification dose" (VD) which is equal to the highest of the three FNP doses.

The VD is used to perform a VDE in which 100 products from each of the three batches are irradiated at the VD. The tolerances for the VDE should be similar to those in the IDE. The irradiated product items are individually tested for sterility and the number of positive tests recorded no more than two positive tests of sterility should appear for each of the batches.

This data is then used to calculate a primary $D_{10}$ value ($PD_{10}$) using the formula $PD_{10}=VD/(2+\log(BB))$, where BB is the batch average bioburden in colony-forming units (CFU).

The present inventors have examined a large number of actual populations and a large series of simulated populations of microorganisms to determine a relationship of the $D_{10}$ required to reduce each population over a wide range of bioburden numbers between that yielding a $10^{-2}$ SAL ($PD_{10}$) and that necessary to reduce the population remaining at the $10^{-2}$ dose to a $10^{-6}$ SAL. The second $D_{10}$ is termed the terminal $D_{10}$ or $TD_{10}$.

Populations A through F comprising distributions of resistance of six different microbial populations, and selected modifications thereof, have found use as challenges in computer evaluations of various dose setting and substantiation methods. Population C is the standard employed in dose setting Method 1 and, as such, was designed to represent a highly severe challenge to the radiation sterilization process; in developing the distribution, measurements of the resistance of constituent microorganisms giving $D_{10}$ values ranging from 1.0 to 4.2 kGy, were carried out with the organisms dried in the presence of organic material, thereby deliberately creating highly effective radiation protective conditions. Population B represents the resistances of the same microorganisms as in Population C but with resistances measured in the absence of organic solutes; overall, it's response to radiation is somewhat greater than that of Population C, the $D_{10}$ range being 0.8 to 3.3 kGy. Theoretical Population A was postulated from Population B to represent a minimal microbial challenge to the radiation sterilization process—it was derived by reducing each of the 9 classes of $D_{10}$ values by around 30% while retaining frequencies of occurrence found for Population B. Clearly, the initial selection of Population A is in keeping with the envisaged microbiological status of candidate products to which a new method of dose setting would be applied. D, E and F are populations which possess resistance distributions that exhibit responses to radiation much less than that of Population C and thus are not relevant in the present context.

The notion of dividing a radiation dose-response curve of a heterogeneous microbial population into two distinct parts was first utilized in the development of Method $VD_{max}$. In taking this activity forward, it was recognized that, subject to passing the VDE at a specified SAL (generally $10^{-2}$), it is solely the response of the microbial population on product surviving at this SAL that sets the sterilization dose to achieve a target SAL somewhat below $10^{-2}$ (generally $10^{-6}$). This terminal response is definable quantitatively by the $D_{10}$ value derived from the linear line joining the two points (log $10^{-2}$, dose at $10^{-2}$), (log $10^{-6}$, dose at $10^{-6}$); its value has been symbolized by the term $TD_{10}$. The upper part of the dose-response curve, occurring above an SAL of $10^{-2}$, is similarly definable through a $D_{10}$ derived from the line joining the points (log bioburden, dose=0), (log $10^{-2}$, dose at $10^{-2}$), its value being symbolized by $PD_{10}$. This analysis of dose-response curves of Population C is the foundation of Method $VD_{max}$ that is now being applied to the substantiation of a range of sterilization doses extending from 15 to 35 kGy; in this context, it has proved to be both a valuable and valid approach (Note, with Method $VD_{max}$, verification is performed at an SAL of $10^{-1}$ and, hence, this SAL is the transition point on the dose-response curve for the calculation of values of $PD_{10}$ and $TD_{10}$ for use with this method).

Heterogeneous microbial populations with an associated heterogeneous radiation response will generally constitute the bioburden present on product prior to sterilization. Such populations inevitably yield values of $TD_{10}$ that exceed those of $PD_{10}$ and, hence, give $TD_{10}/PD_{10}$ ratios that are greater than 1.0. Exceptionally, bioburden may comprise microorganisms of single type exhibiting a homogeneous response to radiation. Homogeneous populations give ratios of 1.0 or, in circumstances where the microorganism's dose-response curve exhibits a shoulder, less than 1.0.

popA

For "Population A" (popA), which is heterogeneous, the expectation is for $TD_{10}/PD_{10}$ ratios to be greater than 1.0 irrespective of the level of bioburden. This was found to be so. $TD_{10}/PD_{10}$ ratios vary systematically over the bioburden range, 0.02 to 1000, taking a value of 2.01 at the lower limit and 1.67 at the upper while passing through a maximum of 2.18 at a bioburden of 0.50. The existence of a maximum is due to the different rates at which values of $TD_{10}$ and $PD_{10}$ increase with increasing bioburden. Rounding up of this maximum to a value of 2.2 provides an initial choice of the $PD_{10}$ coefficient against which values of $TD_{10}/PD_{10}$ ratios derived from populations possessing distributions of resistance other than that of popA can be compared.

popC

Values of $TD_{10}/PD_{10}$ ratios for "Population C" (popC), another heterogeneous microbial population, behave in a manner similar to that found for popA with increasing bioburden. For bioburden levels extending from 0.02 to 1000, ratios range from 1.78 to 1.58 with a maximum of 1.92 at a bioburden of around 0.30. popC is the resistance distribution (so-called Standard Distribution of Resistances) on which dose setting Method 1 is founded and its $TD_{10}/PD_{10}$ ratios are, at comparable bioburden levels, universally less than those of popA, a finding indicating a degree of conservativeness associated with a choice of 2.2 as the $PD_{10}$ coefficient.

popA_MD55 to MD62

These microbial populations comprise a family developed by the modification of popA. Modification involved shifting systematically to the right the frequency of the highest resistance occurring in popA while reversing the displaced frequencies in ascending order within the eight populations. This gave populations with responses to radiation that progressively decrease with increasing MD designator. As all eight MDs are heterogeneous, they gave values of $TD_{10}/PD_{10}$ ratios greater than 1.0. For this group of populations with widely varying resistance distributions, no value of the $TD_{10}/PD_{10}$ ratio was greater than 2.05 for the bioburden range 0.02 to 1000 with the vast majority well below the comparator value of 2.2. In fact, as the overall resistance of the populations increased (in other words, the response to radiation decreased), the ratios approached a value of 1.0, again pointing to the conservative nature of a coefficient of 2.2.

Other Modified Distributions Derived from popA

Another means of developing distributions of resistance varying overall from that of the parent distribution is to progressively sum the resistance probabilities, starting with that which takes the lowest value and proceeding to the highest. This provides populations for which responses to radiation are, to varying degrees, either more than or less than that of the parent population. PopA_MD6 and MD9 is one such pair of populations that respond in this opposite way, popA_MD10 and MD14 is another and popA_MD15 and 20 is a third, the population with the higher numerical designator of the pair showing the lesser response to radiation and the difference in response for the paired populations becoming greater as the designator increases. For those modified populations whose response to radiation is greater than that of popA (MD6, 9 and 15), calculated values of $TD_{10}/PD_{10}$ ratios across the bioburden range 0.02-1000 are all below corresponding values for popA and thus are amply covered by a value of 2.2. In contrast, the populations, which have been modified in a way that provides a proportion of resistant microorganisms in excess of that of popA resulting in a lessened response to radiation, give values of ratios at the low end of bioburden range that are greater than 2.2. For example, a maximum ratio of 2.52 is seen for popA_MD9 at a bioburden of 0.3, 2.76 for MD14 at 0.2 and 3.04 for MD20 at 0.08. Clearly, these findings require consideration in making the final choice for the value of the $PD_{10}$ coefficient.

Miscellaneous Populations

Seven further populations have been studied. Two, created from each of popA and popC, were developed so that the same probability occurred in each resistance class making up the distribution; they were designated popA_even and popC_even, respectively. Two more populations were modifications of popA and popC. They comprised equal probabilities of each of solely the most sensitive and most resistant classes of the populations and were given designates popA_50S_50R and popC_50S_50R. Three populations were homogeneous in nature, each comprising a single type of microorganism having a resistance defined by a $D_{10}$ value of 0.5, 2.5 or 4.2 kGy; they were designated pop_mono 0.5, 2.5 and 4.5, respectively.

All seven populations gave $TD_{10}/PD_{10}$ ratios according to the general expectation noted above. The heterogeneous populations provided a range of values of ratios that varied systematically with changing bioburden level and exhibited a maximum. Furthermore, with the exception of popA_50S_50R at a bioburden of 0.02, ratios took values of less than 2.2. The exception resulted from the presence of an unduly low $PD_{10}$ value at this bioburden level. The homogeneous 'mono' populations all showed $TD_{10}/PD_{10}$ ratios of 1.0.

Simulated experiments, employing mixed suspensions of *B. pumilus* spores and *S. marcescens* cells irradiated at doses ranging from 0.25 to 1.0 kGy, gave the necessary assurance that detection is technically feasible with these radiation doses. They also demonstrated that an Incremental Dose Experiment employing this dose range could yield an array of fraction positive results from which an estimate of the dose to achieve an SAL of $10^{-2}$ could be obtained.

The simulated IDE and VDE have demonstrated that associated procedures, as modified, give successful outcomes. Thus, there is good reason to believe that 'low dose' IDEs and VDEs carried out on product will be technically-feasible, practical procedures from which meaningful and necessary doses can be identified.

The $TD_{10}/PD_{10}$ analysis of popA produced a maximal rounded-up ratio of 2.2 and this value has been set against values of ratios derived from analyses done on a wide variety of populations having substantially different, but often allied, resistance distributions. The general outcome from this comparison is that popC, which has a greater radiation resistance than popA, and most populations with modifications to the resistance distribution of popA provide values of ratios appreciably less than 2.2 over a wide range of bioburden levels. Clearly, this outcome supports strongly the choice of 2.2 as the $PD_{10}$ coefficient and underlines the conservativeness of the value. The exceptions to this finding are certain populations possessing distributions in which there are present higher proportions of microorganisms of high radiation resistance than that in popA. Their presence produces principally increases in the values of $TD_{10}$ which, in turn, give high $TD_{10}/PD_{10}$ ratios.

Given the above exceptions, what has to be considered is the relevance of such distributions to the 'real world'. At present this is a judgment decision, although it has to be said that, in the light of the stipulated manufacturing conditions and the controls to be imposed on them, the occurrence on product prior to sterilization of microbial populations having a significant number of microorganisms of high radiation resistance is highly unlikely. Moreover, the results of the VDEs will act as a check for their absence. If such microorganisms do occur, they will have to present at a specific bioburden in a proportion in excess of that of popA level for the $PD_{10}$ coefficient of 2.2 to be invalid.

$TD_{10}$ is thus assumed to be 2.2 times $PD_{10}$. The sterilization dose to achieve a $10^{-6}$ SAL is then calculated by adding four $TD_{10}$ doses to the VD, in other words sterilization dose equals VD plus (4*$TD_{10}$).

The sterilization dose is thus the dose used to sterilize the devices in question and provides a sterility assurance level of $10^{-6}$. The method is recommended for extremely low average bioburdens of five CFU or below. It is useful for sterilization of delicate drugs and radiation sensitive devices.

Proteins are particularly difficult to sterilize without damage. One particular area of concern for the inventors is the sterilization of blood proteins and plasma proteins. The source of the proteins may be natural (i.e. human, animal), synthetic or recombinant. Blood protein/plasma protein serves as a transport molecule for lipids, hormones, vitamins and metals. They also serve as enzymes, complement components, protease inhibitors, and kinin precursors. Blood protein/plasma protein includes, but is not limited to, albumin, ancrod, batroxobin, collagen, ecarin, elastin, epinephrine, Factor X/Xa, Factor VII/VIIa, Factor IX/IXa, Factor XI/XIa, Factor XII/XIIa, fibrin, ficolin, fibrinogen, fibronectin, gelatin, globin, haptoglobin, hemoglobin, heparinase, inhibin, insulin, interleukin, lamininthrombin, platelet surface glycoproteins, prothrombin, selectin, thrombin, transferin, von Willebrand Factor, vasopressin, vasopressin analogs, procoagulant venom, platelet activating agents and synthetic peptides having hemostatic activity.

The present inventors are also concerned with sterilization of polymers, and in particular polymers useful in preparing the fabric substrates in wound dressings, which include, without limitation, collagen, calcium alginate, chitin, polyester, polypropylene, polysaccharides, polyacrylic acids, polymethacrylic acids, polyamines, polyimines, polyamides, polyesters, polyethers, polynucleotides, polynucleic acids, polypeptides, proteins, poly (alkylene oxide), polyalkylenes, polythioesters, polythioethers, polyvinyls, polymers comprising lipids, and mixtures thereof. Preferred fibers comprise oxidized regenerated polysaccharides, in particular oxidized regenerated cellulose. The methods of the present invention are expected to be quite useful with the preceding polymers and proteins.

While the invention has been particularly described in connection with specific embodiments thereof, it is to be understood that this is by way of illustration and not of limitation, and that the scope of the appended claims should be construed as broadly as the prior art will permit.

What is claimed is:

1. A method for sterilizing objects with radiation, the method comprising the steps of determining a dosage of radiation sufficient to ensure sterilization to a sterility assurance level of $10^{-6}$ and then applying said dosage of radiation to the objects, and wherein the step of determining said dosage includes the steps of:
   determining a bioburden upon one or more samples of the objects;
   determining an estimate of the dose that results in a probability of 0.01 of a surviving microorganism on the objects by testing a quantity of samples of the objects at varying dosage levels of radiation to determine a dosage below which not at all samples are sterilized and above which they are sterilized;
   confirming the estimate of the dose that results in a probability of 0.01 of a surviving microorganism on the objects by testing a quantity of samples of the objects at the dose that was estimated; and
   calculating a dosage for the sterility assurance level of $10^{-6}$ by adding a factor to the dose that was confirmed to result in a probability of 0.01 of a surviving microorganism on the objects and wherein the factor is proportional to the dose that yields a probability of 0.01 of a surviving microorganism on the objects and inversely proportional to a log of the bioburden, wherein the factor equals $PV*(CD/(2+\log(BB)))$, wherein PV represents a proportionality value, CD represents the dose that has been confirmed to result in the selected probability of a surviving organism on the objects and BB represents the bioburden in colony-forming units.

2. A method according to claim 1 wherein the bioburden is equal or less than 20 CFU.

3. A method according to claim 1 wherein the bioburden is equal or less than 5 CFU.

4. A method according to claim 1 wherein the quantity is 100 samples of the objects for confirming that the estimated dose results in a probability of 0.01 of a surviving microorganism on the objects.

5. A method according to claim 1 wherein PV ranges from 1.0 to 10.0.

6. A method according to claim 1 wherein PV is 2 or greater.

7. A method according to claim 6 wherein PV is at least 2.2.

8. A method according to claim 1 wherein PV ranges from 2 to 3.

9. A method according to claim 1 wherein the object comprises a protein.

10. A method for determining a sterilization dose for an object comprising determining a factor equal to $PV*(CD/(2+\log(BB)))$, wherein PV represents a proportionality value, CD represents the dose that has been confirmed to result in a probability of 0.01 of a surviving microorganism on the object and BB represents the bioburden in colony-forming units.

11. The method of claim 1 or 10 wherein $PV=TD_{10}/PD_{10}$ and wherein $TD_{10}$ represents a $D_{10}$ value observed to reduce a microorganism population to a $10^{-6}$ sterility assurance level (SAL) from a $10^{-2}$ SAL and $PD_{10}$ represents the $D_{10}$ value observed to reduce a microorganism population to a $10^{-2}$ SAL.

12. A method for sterilizing objects with radiation, the method comprising the steps of determining a dosage of radiation sufficient to ensure sterilization to a desired sterility assurance level and then applying said dosage of radiation to the objects, and wherein the step of determining said dosage includes the steps of:
   determining a bioburden upon one or more samples of the objects;
   determining an estimate of the dose that results in a selected probability of a surviving microorganism on the objects by testing a quantity of samples of the objects at varying dosage levels of radiation to determine a dosage below which not at all samples are sterilized and above which they are sterilized;
   confirming the estimate of the dose that results in the selected probability of a surviving microorganism on the objects by testing a quantity of samples of the objects at the dose that was estimated; and
   calculating a dosage for the desired sterility assurance level by adding a factor to the dose that was confirmed to result in the selected probability of a surviving microorganism on the objects and wherein the factor is proportional to the dose that yields the selected probability of a surviving microorganism on the objects and inversely proportional to a log of the bioburden, where the factor is represented by a mathematical expression $PV*(CD/(2+\log(BB)))$, wherein PV represents a proportionality value, CD represents the dose that has been confirmed to result in the selected probability of a surviving organism on the objects and BB represents the bioburden in colony-forming units.

13. A method for determining a sterilization dose for an object comprising determining a factor equal to $PV*(CD/(2+\log(BB)))$, wherein PV represents a proportionality value, CD represents the dose that has been confirmed to result in a selected probability of a surviving microorganism on the object and BB represents the bioburden in colony-forming units.

14. The method of claim 13 wherein $PV=TD_{10}/PD_{10}$ and wherein $TD_{10}$ represents a $D_{10}$ observed to reduce a microorganism population to a $10^{-6}$ sterility assurance level (SAL) from a $10^{-2}$ SAL and $PD_{10}$ represents the $D_{10}$ value observed to reduce a microorganism population to a $10^{-2}$ SAL.

15. A method for determining a sterilization dose to achieve a $10^{-6}$ sterility assurance level (SAL) for an object which comprises the steps of (i) determining a sterilization verification dose (VD) for the object for a $10^{-2}$ SAL and (ii) adding to the VD value, a value equal to four times the value of $TD_{10}$ where $TD_{10}$ represents a $D_{10}$ observed to reduce a microorganism population to a $10^{-6}$ SAL from a $10^{-2}$ SAL and wherein $TD_{10}$ equals to $PV*(VD/(2+\log(BB)))$, wherein PV represents a proportionality value, VD represents the dose that has been confirmed to result in a probability of 0.01 of a surviving microorganism on the objects and BB represents the bioburden in colony-forming units.

16. The method of claim 15, wherein the VD value is determined by the steps of:
  determining a bioburden upon one or more samples of the objects;
  determining an estimate of the dose that results in a probability of 0.01 of a surviving microorganism on the objects by testing a quantity of samples of the objects at varying dosage levels of radiation to determine a dosage below which not at all samples are sterilized and above which they are sterilized;
  confirming the estimate of the dose that results in a probability of 0.01 of a surviving microorganism on the objects by testing a quantity of samples of the objects at the dose that was estimated.

\* \* \* \* \*